United States Patent [19]

Boulware

[11] Patent Number: 4,769,452
[45] Date of Patent: Sep. 6, 1988

[54] PRODUCTION OF PURITY BENZO-C-PHENANTHRIDINE ALKALOID SALTS

[75] Inventor: Richard T. Boulware, High Point, N.C.

[73] Assignee: Vipont Laboratories, Inc., Fort Collins, Colo.

[21] Appl. No.: 63,745

[22] Filed: Jun. 18, 1987

Related U.S. Application Data

[63] Continuation of Ser. No. 827,143, Feb. 7, 1986, abandoned, which is a continuation-in-part of Ser. No. 596,589, Apr. 4, 1984, abandoned.

[51] Int. Cl.⁴ ............... C07D 221/18; C07D 491/056; C07D 491/153
[52] U.S. Cl. ..................... 540/476; 546/41; 546/48; 546/61; 424/195.1
[58] Field of Search ............ 546/41, 48, 61; 540/476; 424/195.1; 514/279, 280, 284, 285

[56] References Cited

U.S. PATENT DOCUMENTS

| | | | |
|---|---|---|---|
| 3,843,788 | 10/1974 | Iwasa et al. | 424/195 |
| 3,849,561 | 11/1974 | Iwasa et al. | 424/258 |
| 4,145,412 | 3/1979 | Ladanyi | 424/58 |
| 4,335,110 | 6/1982 | Collins | 424/145 |
| 4,376,115 | 3/1983 | McCrorey | 424/145 |
| 4,406,881 | 9/1983 | Ladanyi | 424/49 |

FOREIGN PATENT DOCUMENTS

| | | | |
|---|---|---|---|
| 2755577 | 6/1979 | Fed. Rep. of Germany | 546/41 |
| 2856577 | 6/1980 | Fed. Rep. of Germany | 546/41 |
| 0022355 | 7/1970 | Japan | 514/279 |
| 2078109 | 1/1982 | United Kingdom | 514/279 |
| 0495311 | 4/1976 | U.S.S.R. | 546/41 |
| 0931186 | 6/1982 | U.S.S.R. | 514/280 |

OTHER PUBLICATIONS

Mitscher et al., Lloydia, vol. 41, No. 2, pp. 145–150 (3–4/1978).
Gheorghiu et al., Chemical Abstracts, vol. 74, 110201b (1971).
Loyzuk et al., Chemical Abstracts, vol. 87, 78524q (1977).
Vichkanova et al., Chemical Abstracts, vol. 89, 100745c (1978).
Hladon et al., Chemical Abstracts, vol. 92, 15307d (1980).

Primary Examiner—Donald G. Daus
Assistant Examiner—Diana G. Rivers
Attorney, Agent, or Firm—Eric P. Schellin

[57] ABSTRACT

A method of extracting benzo-c-phenanthridine alkaloids from plants of the families Papaveraceae, Fumariaceae, and Berberidaceae, comprising grinding the plant, extracting the ground plant with acidulated methanol or acidulated ethanol, precipitating the extract with an acid salt soluble in the solvent used, redissolving the precipitated salt in water, adding sufficient acid to form a precipitate, and collecting the precipitate so formed.

9 Claims, No Drawings

PRODUCTION OF PURITY BENZO-C-PHENANTHRIDINE ALKALOID SALTS

This application is a continuation of application Ser. No. 827,143, filed 2/7/86, which is a continuation-in-part of Ser. No. 596,589, filed Apr. 4, 1984, both now abandoned.

BACKGROUND OF THE INVENTION

This invention relates to a method for recovering active benzo-c-phenanthridine alkaloids from plants containing these compounds.

*Sanguinaria canadensis*, Linn (family Papveracea) is commonly known as bloodroot, redroot, puccoon, teterwort, etc., and is a perennial herb native to North America. The plant and its juices have been used for various purposes in pre-historical and historical times. The plant has been used, in particular, as a folk remedy. The plant has generally been used whole, either undried (fresh) or dried. The usual procedure is to powder the dried plant and mix it with a carrier. This folk remedy has been tried for such conditions as asthma, bronchitis, dysentery, ringworm, and a substantial list of other ailments.

The principal use of Sanguinaria has been as a stimulant expectorant in cough syrups and in homeopathic medicine. In more recent years it has been used as an antiplaque agent in dentifrices and oral rinses.

An early patent, U.S. Pat. No. 209,331, discloses the use of bloodroot, zinc chloride, and kerosene oil in equal proportions for treating open sores. U.S. Pat. No. 433,257, describes a salve of pulverized bloodroot, armenian bole, powdered rosin, lard, and Stockholm tar for use in the treatment of piles. U.S. Pat. No. 2,344,830, discloses the use of a mixture of zinc chloride, stibnite, and bloodroot to fix and outline diseased tissue for excision by surgery.

More recently, it has been discovered that extracts of sanguinaria and other plants of the families Papaveraceae, Fumariaceae, and Berberidaceae such as *Macleaya cordata, Macleaya Microcarpa, Bocconia frutescens, Corydalis sevctcozii, C. ledebouni, Argemone mexicanus*, and *Chelidonium majus* contain benzo-c-phenanthridine alkaloids which are believed to have valuable properties in the control of dental plaque formation, conditioning oral tissue, as well as in preventing and treating gingivitis, periodontitis, and mouth odors.

The pure chemicals sanguinarine, chelerythrine, protopine, chelerubine, chelilutine, sanguilutine, macarpine, sanguirubine, allocryptopine, homochelidonene, and berberine, can be isolated from plants other than Sanguinaria. They are also available, although rarely, from some chemical supply houses. Semi-purified forms of the alkaloids are commercially available; these are generally referred to as sanguinarine nitrate and sanguinarine sulfate. These "salts" are the salts of the mixed alkaloids of the plant Sanguinaria: namely, sanguinarine, chelerythrine, and protopine. While few references can be found in the literature regarding the usage of any of the pure benzophenanthridine alkaloids, plants containing such compounds have been used for a wide variety of medical ailments.

Several patents have disclosed the use of extracts of Sanguinaria for such purposes, notably U.S. Pat. No. 4,145,412; U.K. Patent No. 2,042,336; U.S. Pat. No. 4,376,115; U.S. Pat. No. 4,406,881; German Offen. No. 2,907,406; Belgian patent No. 888,843. These patents describe the use of Sanguinaria extracts as antimicrobial agents as well as mouth treating agents.

The prior art cited above describes a method of extracting active ingredients from *Sanguinaria canadensis* by extracting out of ground bloodroot with methanol for at least 24 hours at an elevated temperature, filtering the liquid extract obtained, evaporating the extract to dryness, dissolving the dried residue in chlorofom, adjusting the chloroform solution to an acid pH by the addition of hydrochloric acid, filtering the acidified extract, evaporating it to dryness, and dissolving the dried residue in glycerine for mixing with a carrier.

SUMMARY OF THE INVENTION

The present invention is directed to a more refined method for a valuable extract from plants of the families Papaveraceae, Fumariaceae, and Berberidaceae such as *Sanguinaria canadensis, Macleaya cordata, Corydalis seoctvozzii, C ledeborini, Argemone mexicanus, Chelidonium majus, Bocconia frutescens,* and mixtures thereof which extract has been identified as a misture of benzo-c-phenanthridine alkaloids.

The benzo-c-phenanthridine alkaloids which have been identified in Sanguinaria include sanguinarine, chelirubine, sanguirubine, chelilutine, chelerythrine, and sanguilutine. Berberine, a related alkaloid has also been identified.

In the process of the present invention, methanol, ethanol or mixtures of Deionized water and alcohol acidified to a pH of 1 to 3 can be used as an extractant. An acid salt is then used as a precipitating agent. These steps yield an improved product which has a high degree of purity and an acceptable yield.

DETAILED DESCRIPTION OF THE INVENTION

EXAMPLE I

The extraction is performed in two phases. In phase one, 25 kg. of ground bloodroot plant is placed into an extraction vessel. Next, 37.5 liters of methanol which has been acidulated with 37.5 grams of citric acid and 375 ml. HCl is added to the vessel. The vessel is left to stand untouched for 16–24 hours, after which time 25 liters of the extract is pulled off by a vacuum pump running at about 150 mm Hg vacuum. At this point, another 25 liters of methanol acidulated with 25 grams of citric acid and 250 ml. HCl is added to the extraction vessel, and this is allowed to stand for 6–8 hours. Another 25 liters of extract are withdrawn and added to the 25 liters collected above. To this combined 50 liters is added 2 liters of 27% solution of zinc chloride in methanol or 27% zinc chloride in water. The precipitate thus formed is allowed to sit at room temperature for 16–18 hours. The precipitate is collected and dried in an oven set at 70° C.

In phase two, the dried precipitate from phase one is weighed and redissolved in enough of a 2.5% solution of citric acid to effect a concentration of 1 gram of precipitate to 40 ml. of solution. This suspension is heated to about 70° C. and filtered hot. The collected hot filtrate is then combined with enough NaCl (USP) to effect a concentration of about 3.68 grams NaCl to 100 ml. filtrate. Alternatively, potassium chloride can be used in the same amount as the sodium chloride. The precipitate thus formed is allowed to stand at room temperature for 16–18 hours. The precipitate is filtered and placed into an oven, set at 60° C., to dry, or is dried in vacuo. The dried precipitate is then ground, weighed, and packaged for further use.

Instead of zinc chloride in phase one, step three, other acid salts which are soluble in methanol can be used. Such salts include zinc sulfate, zinc iodide, zinc nitrate, and other zinc acid salts which are soluble in the solvent used, either ethanol or methanol. If water-alcohol is used as the extractant then sodium chloride may be used as the precipitating agent.

EXAMPLE II

Phase 1

One kg. of bloodroot is extracted with 3.0 liters of acidulated methanol (1% HCl, 0.5% citric acid) for three days over dry sea sand and glass wool. The extract is forced, using vacuum or air pressure, into a separate container. Approximately two-thirds of the methanol is recovered in the transfer. If hot methanol is used the extraction may be completed in 8 hours.

For every liter of extract transferred, 40 ml. of a concentrated acidulated salt solution is added as a precipitating agent. The precipitated extract is digested for 27 hours and collected as a filter cake by vacuum filtration. The filter cake is approximately 25% solids and 75% methanol. This material is dried in wax paperlined steel pans at 50° to 60° C. for 48 to 72 hours until dry and brittle. Once dry, this material is ground to a fine powder.

PHASE TWO

One kg. of fine dry powder from phase one and 50 grams of citric acid are dissolved as completely as possible in 20 liters of water.

This material is filtered to remove water insolubles (down to the 0.5-2 micron range), and the filtrate is collected into a vessel containing a precipitating agent such as sodium chloride. The collecting vessel must be frequently agitated. The precipitate so generated is left to digest overnight, and the precipitate is collected as a filter cake which is dried in wax paperlined steel pans at 5 to 40° C. This drying step takes approximately 24 hours. The yield is about 50% of that obtained in phase one.

The dried extract can then be dissolved in a suitable carrier, such as glycerine, for incorporation into products for oral use such as mouthwash, toothpaste, breath spray and the like.

EXAMPLE III

Example II is repeated using powdered *Macleaya cordata* as the plant material, and acidulated ethanol as the extracting solvent. The end product was a mixture of sanguinarine chloride and chelerythrine chloride.

In order to form the nitrate of the sanguinaria, nitric acid is used in place of hydrochloric acid. Likewise, to form the sulfate, sulfuric acid can be used in place of hydrochloric acid.

The salts used were extracts of sanguinaria and macleaya as obtained in Example I.

Solutions of the extracts were made with sterile pH 6.5 deionized water. Concentrations were produced in 30 fold concentrations, so that the final concentration in the wells would be 32, 28, 24, 20, 16, 12, 8 and 4 ug/ml.

Bacterial media CYE2 was used in this determination. This media contains caseamino acids (25 g), yeast extract (1.0 g), glucose (5.0 g). 10 ml of 200 nM MgSO$_4$, 100 ml of 200 nM potassium phosphate buffer pH 7.0, and 890 ml deionized water. The medium was adjusted to pH 6.5 and filter sterilized with 0.22 micron membrane filters. The medium was made in single strength concentration for culture growth and double strength for minimum inhibitory concentration determination.

Each well of a sterile microtitre plate received 0.09 ml of CYE2 media as a two-fold concentrate, 0.01 ml of a 24 hour culture of *S. mutans* adjusted to approximately 10,000,000 colony forming units per ml, and 0.10 ml of the approximate concentration of the test agent. Five replicates for each concentration of each test agent were cultured. The plates were then incubated at 37° C. for 24 hours. After incubation, the plates were scored as growth or no growth.

Growth was observed in the 4, 8, and 12 ug/ml wells for both compounds, and no growth was observed at higher concentrations. It appears from the above that both compounds have similar MIC values with a dose for both agents at greater that 12 ug/ml and less than 16 ug/ml.

What is claimed is:

1. A method for extracting benzo-c-phenanthridine alkaloids from plants of the families Papaveraceae, Fumariaceae, and Berberidaceae, comprising
   grinding the plant, extracting the ground plant with a solvent selected from the group comprising acidulated methanol, acidulated ethanol, acidulated methanol-water solutions, acidulated ethanol-water solution, and mixtures thereof, precipitating the extract with a zinc salt which is soluble in the solvent, redissolving the precipitated salt in water, adding sufficient acid to form a precipitate, and collecting the precipitate so formed.

2. The method of claim 1 wherein the plants are selected from the group consisting of *Sanguinaria canadensis, Macleaya cordata, Macleaya microcarpa, Carydalis sevctvozii, C. ledebouni, Bocconia frutescens,* and *Chelidonium majus.*

3. The method of claim 2 wherein the plant is *Sanguinaria canadensis.*

4. The method of claim 2 wherein the plant is *Macleaya cordata.*

5. The method of claim 2 wherein the plant is *Macleaya microcarpa.*

6. The method of claim 1 wherein the benzo-c-phenanthridine alkaloids recovered are selected from the group consisting of sanguinarine, chelirubine, protopine, macarpine, allocrystopine homochelidonine, berberine, sanguirubine, chelilutine, chelerythrine, sanguilutine, and mixtures thereof.

7. The method of claim 1 wherein the acid salt is selected from the group consisting of zinc sulfate, zinc chloride, zinc iodide, zinc nitrate and mixtures of zinc salts and sodium chloride.

8. The method of claim 1 wherein the precipitate is treated with ammonium hydroxide to remove residual zinc ion from the precipitate.

9. The method of claim 8 wherein the precipitate treated with ammonium hydroxide is filtered from the solution and treated with an acid to form the desired acid salt.

* * * * *